United States Patent

Sakuma et al.

Patent Number: 5,807,233
Date of Patent: Sep. 15, 1998

[54] METHOD OF ALLEVIATING PAIN USING A HOW DENSITY MAGNETIC FIELD

[75] Inventors: Tetsuo Sakuma, Suita; Akihiro Mori, Kanazawa, both of Japan

[73] Assignee: Shinfuji Kogyo Kabushiki Kaisha, Osaka, Japan

[21] Appl. No.: 252,363

[22] Filed: Jun. 1, 1994

[30] Foreign Application Priority Data

Jun. 3, 1993 [JP] Japan .................................. 5-172001

[51] Int. Cl.⁶ ............................ A61N 1/42; A61B 17/52
[52] U.S. Cl. ................................................................ 600/15
[58] Field of Search ........................................... 600/9–15

[56] References Cited

U.S. PATENT DOCUMENTS 3,921,620  11/1975  Nakayama .............................. 600/15
4,587,956  5/1986  Griffin et al. .............................. 600/15
5,387,176  2/1995  Markoll ...................................... 600/14

FOREIGN PATENT DOCUMENTS 1-227767  9/1989  Japan .
1-227768  9/1989  Japan .

Primary Examiner—John P. Lacyk
Assistant Examiner—Samuel Gilbert
Attorney, Agent, or Firm—Armstrong, Westerman, Hattori, McLeland & Naughton

[57] ABSTRACT

The present invention relates to use of faint magnetism of 2–20 gauss in therapy of aches and a therapy method of the aches by the faint magnetism.

The present invention further relates to a magnetic therapy tool with faint magnetism of 2–20 gauss.

5 Claims, 5 Drawing Sheets

METHOD OF ALLEVIATING PAIN USING A HOW DENSITY MAGNETIC FIELD

BACKGROUND OF THE INVENTION

1. Field of the Invention

The present invention relates to use of faint magnetism in therapy of aches, such as arthritis, low back pain and melagra, and a therapy method of the aches by faint magnetism.

The present invention further relates to a therapy tool with faint magnetism effective for the aches.

2. Description of the Prior Art

Thermotherapy, cooling therapy and pharmacotherapy are known to be effective for arthritis, herniated nucleus pulposus, osteoarthritis of the spine. The thermotherapy is taken most frequently among those kinds of therapy. The thermotherapy uses electromagnetic waves, such as ultrashort waves and waves shorter than ultrashort waves. Heat energy given by the electromagnetic waves influences directly γ-fibers of muscle spindle to reduce responsibility to inflammation. Such thermotherapy using electromagnetic waves is disclosed in, for example, Japanese Patent Laid-Open Hei 1-227767 and Hei 1-227768.

SUMMARY OF THE INVENTION

The object of the present invention is to provide use of faint magnetism effective for therapy or removal of aches, such as arthritis, low back pain and melagra without direct influences on normal cells.

Another object of the present invention is to provide a therapy method of the aches by faint magnetism.

Another object of the present invention is to provide a therapy tool with faint magnetism effective for the aches.

The present invention relates to use of faint magnetism of 2–20 gauss in therapy of aches and a therapy method of the aches by the faint magnetism.

The present invention further relates to a magnetic therapy tool with faint magnetism of 2–20 gauss.

BRIEF DESCRIPTION OF THE DRAWINGS

FIG. 2 is a front view of a human body to explain a position where a magnetic band or belt is put on.

FIG. 3 is a back view of a human body to explain a position where a magnetic belt or band is put on.

DETAILED DESCRIPTION OF THE INVENTION

Figure 1A:
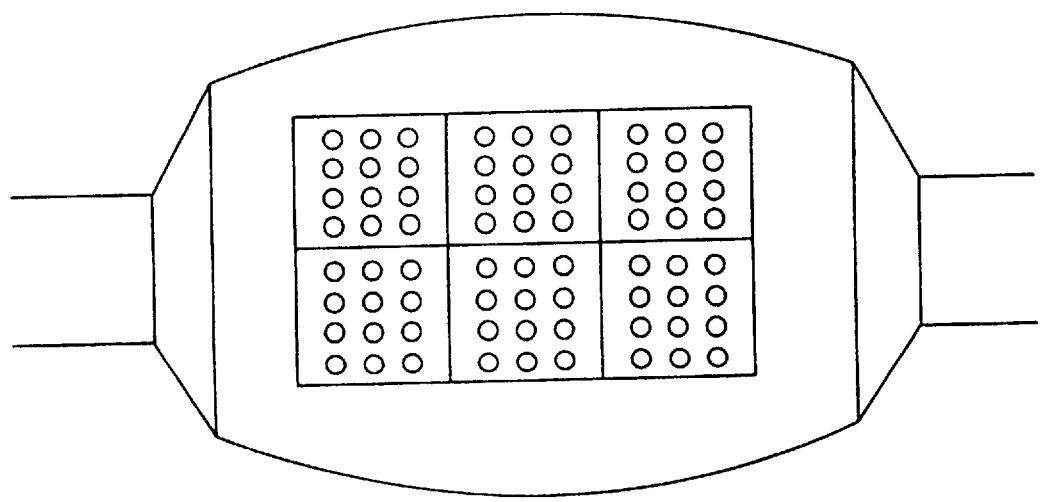
FIG. 1A is a partially schematic illustration of a magnetic belt.

The present invention relates to use of faint magnetism of 2–20 gauss in therapy of aches and a therapy method of the aches by the faint magnetism.

The present invention further relates to a magnetic therapy tool with faint magnetism of 2–20 gauss.

The present inventions are based on finding that aches, for example, arthritis of wrist or elbow, low back pains, such as herniated nucleus pulposus, and osteoarthritis of the spine, are extinguished by exposing the ache-diseased portion to faint magnetism of 2–20 gauss.

The time necessary for recovery depends on whether the ache symptom is serious or slight. It may take only three days to recover. It may take 20 to 30 days to recover. It has been recognized that once the ache diseases as above mentioned are removed or extinguished by application of the present invention, these diseases scarcely ever return.

Magnetism applied to the ache-disease parts has a magnetism strength of 20 gauss or less, preferably 15 gauss or less, more preferably 10 gauss or less. Such a faint magnetism is conventionally recognized to be weak enough not to affect human body adversely. In particular magnetism strength of 10 gauss or less is a standard value to judge whether magnetism is leaking or not in a linear motor car which is under research and development in Japan, because such a faint magnetism is so weak so that a human body is hardly affected adversely. In spite of such conventional recognition, the present inventors have found that such faint magnetism is effective for lessening, extinguishing and recovering from aches, such as arthritis, low back pain and melagra. However when the magnetism is too small, for example, about 1 gauss, it is not effective for extinguish the aches. Therefore it is preferable that magnetism of 2 gauss or more is applied. Surprisingly, more effective effects can be achieved when not N-polar but S-polar faint magnetism is applied to diseased parts, the reason for which is not clear.

A magnetic material used in the present invention is not limited insofar as the material itself emits magnetism. Such a material as used in the present invention may be exemplified by magnetites, magnetic metals, magnetic resins and magnetic fibers.

The magnetites means iron ore having magnetism conventionally present on the earth. The iron ore is isotropic and has magnetism at various levels. When the iron ore is broken into small pieces, the strength of magnetism becomes weak.

The magnetic metal is a magnetism-provided metal including alloy, which is anisotropic.

The magnetic resins means materials in which magnetic materials, such as ferrite, are added into synthetic resins, such as polyethylene. The magnetic resins may be treated in a manner similar to the magnetites.

The magnetic fibers mean, for example, fibers containing magnetic materials therein, fibers keeping magnetic materials on the surface thereof, or fibers in the network of which magnetic materials are included. Other fibers known as a magnetic fiber may be used. These fibers are generally used in a form of cloth, which is cut into a desired piece.

The magnetic materials, for example, the magnetites and magnetic metals, are processed into small pieces of about 4–5 mm easy to handle, so that they will emit magnetism of 2–20 gauss. These pieces of the magnetic material are arranged on a belt or a pad, or something like that. Such a belt or a pad is applied to an ache-diseased part caused by arthritis, herniated nucleus pulposus and osteoarthritis of the spine to reduce and extinguish the ache. In the case of cloth made of the magnetic fibers, a piece of the cloth may be directly taped on an ache-diseased part. The cloth may be processed to give a belt or a band.

The magnetites, magnetic metals and magnetic resins may be used in a form of a magnetic fluid composition or an ointment composition.

In the present invention, even if the magnetic materials are used in any form or shape, it is desirable that magnetism is within the range between 2 gauss and 20 gauss. However magnetism of more than 20 gauss or less than 2 gauss may be emitted partially because such magnetic materials as emit the magnetism of more than 20 gauss or less than 2 gauss may be included almost inevitably depending on producing conditions, a kind of raw materials or some other factors.

When the magnetic materials are anisotropic, they are arranged so that S-polar magnetism will be applied to ache-diseased parts.

After aches, such as arthritis, herniated nucleus pulposus and osteoarthritis of the spine, are reduced and extinguished by application of the faint magnetism to the aches according to the present invention, it is preferable that the faint magnetism is further applied for 10–30 days. Thereby the ache diseases can be prevented more completely from returning.

Further a magnetic therapy tool of the present invention is also found to be effective for stiffness in shoulders. The tool is applied to a stiffness part to reduce and remove the stiffness in the shoulders.

The present invention is further explained below with Examples, but these are shown with no significance in restricting the embodiments of the invention.

A magnetic belt or a magnetic band used in Examples 1–4 was prepared as follows.

Figure 1B:
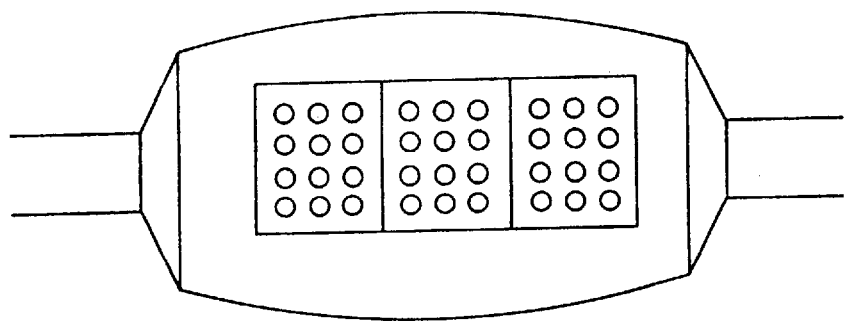
FIG. 1B is a partially schematic illustration of a magnetic band.

Magnetite was broken into pieces having particle size of about 4 mm–5 mm. Twelve pieces were put into a pouch made of poly(vinyl chloride) having a size of 3 cm square. Six pouches were arranged to give a magnetic belt as shown in FIG. 1(a). Three pouches were arranged to give a magnetic band as shown in FIG. 1(b). The belt or the band was applied to an ache-diseased part caused by arthritis, herniated nucleus pulposus or osteoarthritis of the spine, so that the ache-diseased part was exposed in the magnetic field of about 10 gauss in mean strength of magnetism.

EXAMPLE 1

The name of a disease was arthritis of right hand. The patient was a male of 45 years old, suffering from an ache of right hand wrist caused by a sport at the beginning of October in 1992.

Figure 2:
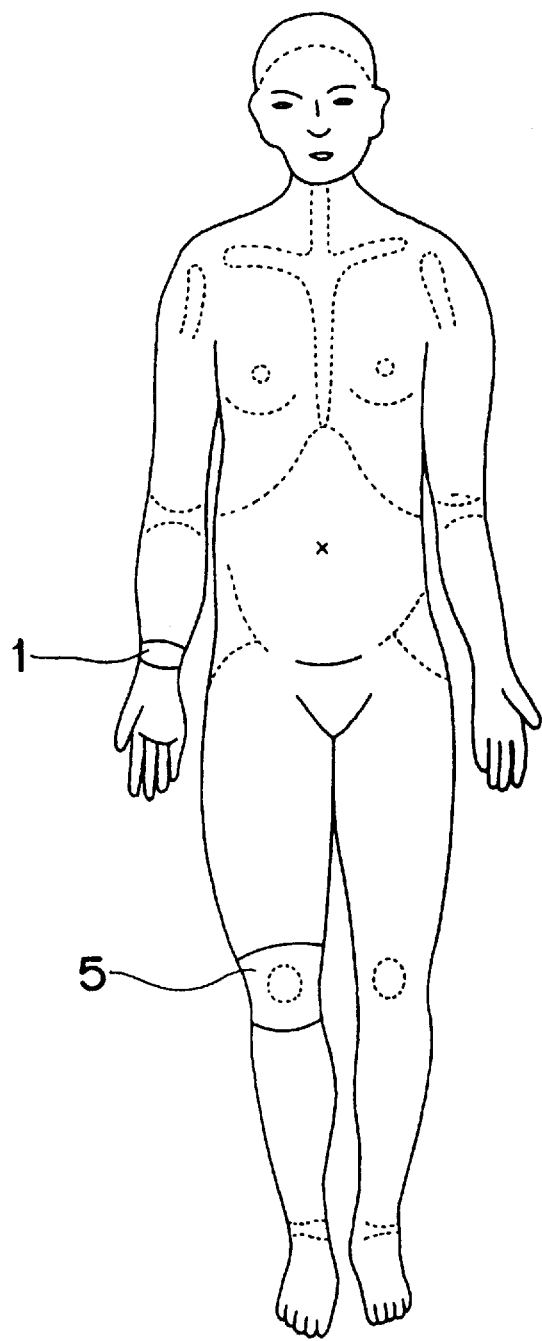

The magnetic band was applied around the right hand wrist (1) as shown in FIG. 2. After 7 days had passed, the ache was gradually reduced. After 20 days had passed, the ache was completely extinguished.

EXAMPLE 2

The name of a disease was herniated nucleus pulposus. The patient was a male of 51 years old, suffering from a low back pain from January in 1993.

Figure 3:
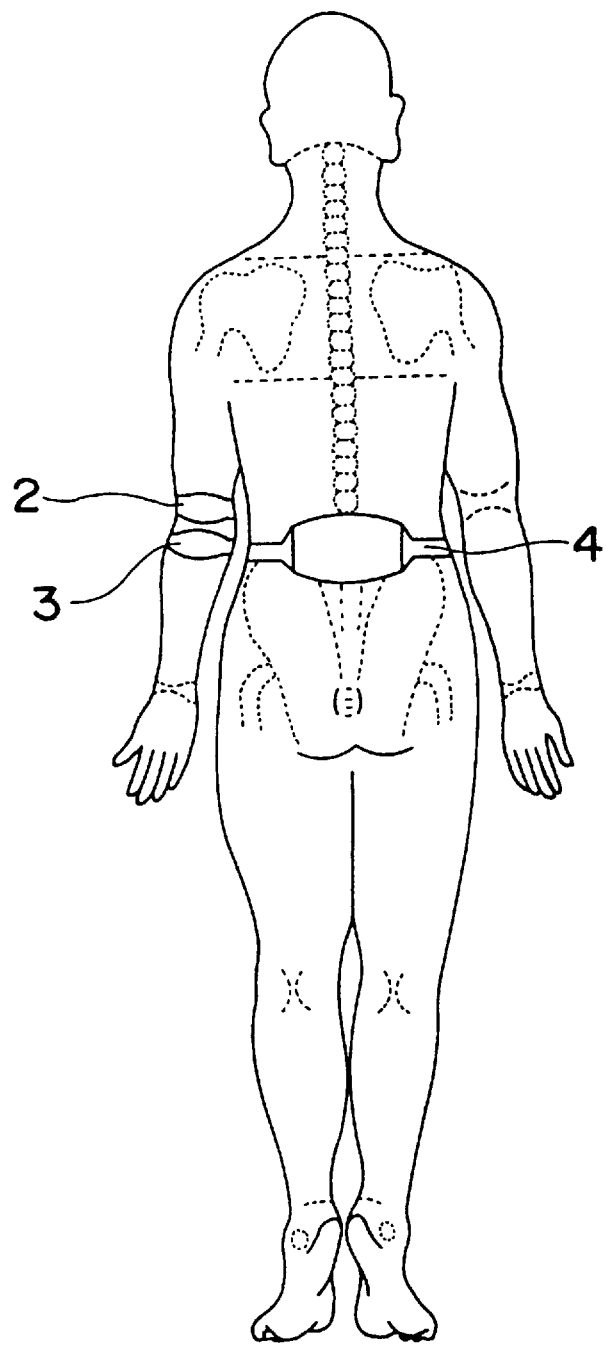

The magnetic belt was applied around the waist (4) as shown in FIG. 3. After 2 weeks had passed, the low back pain was completely extinguished.

EXAMPLE 3

The name of a disease was osteoarthritis of the spine. The patient was a male of 70 years old, suffering from a low back pain from the beginning of February in 1993.

The magnetic belt was applied around the waist (4) as shown in FIG. 3. After 3 weeks had passed, the low back pain was completely extinguished.

EXAMPLE 4

The name of a disease was anconitis of left hand elbow. The patient was a male of 58 years old, suffering from an ache of left elbow caused by a sport on Mar. 4 in 1993.

The magnetic band was applied to the upper and lower portions (2) and (3) of the elbow as shown in FIG. 3. After 3 days had passed, the ache was completely extinguished.

EXAMPLE 5

Figure 4:
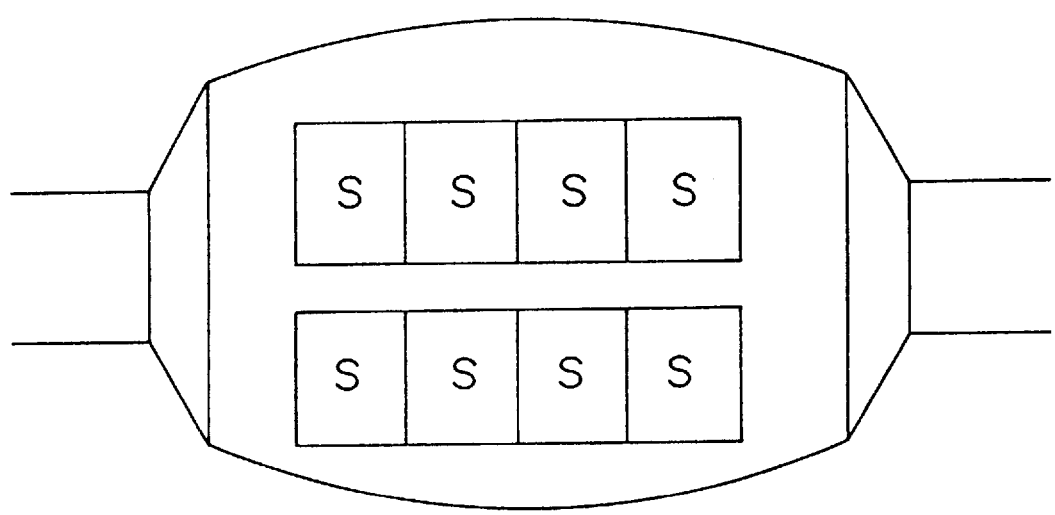
FIG. 4 is a partially schematic illustration of another magnetic belt.

In this Example, 8 pieces of magnetic metal having a size of 20 mm (length)×14 mm (width)×5 mm (thickness) was arranged in two lines (4 pieces per line) to prepare a magnetic belt, as shown in FIG. 4. The magnetic metal used was anisotropic. The pieces of magnetic metal were arranged so that S-polar magnetism would be applied to a diseased part.

The name of a disease was herniated nucleus pulposus. The patient was a male of 50 years old, suffering from a low back pain from January in 1993. A mean strength of magnetism applied was approximately 10 gauss.

The magnetic belt was applied around the waist (4) as shown in FIG. 3. After 20 days had passed, the low back pain was completely extinguished.

EXAMPLE 6

Figure 5:
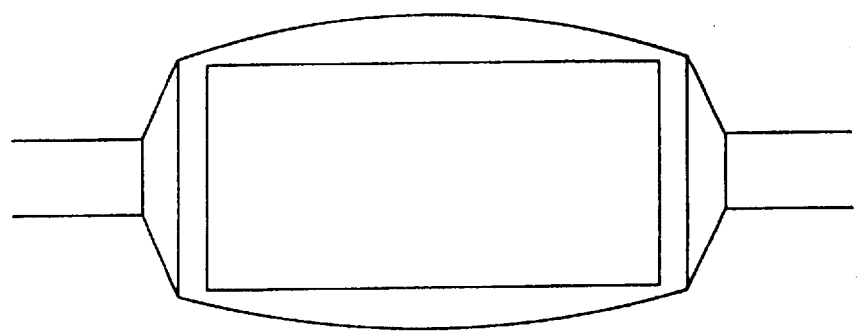
FIG. 5 is a partially schematic illustration of another magnetic band.

In this Example, a cloth made of magnetic fibers having a size of 6 cm (length)×12 cm (width) was arranged to prepare a magnetic band, as shown in FIG. 5. A mean strength of magnetism applied was approximately 10 gauss.

The name of a disease was arthritis of right knee. The patient was a male of 61 years old, suffering from an ache of right knee caused by a sport at the beginning of October in 1993.

The magnetic band was applied around the right knee (5) as shown in FIG. 2. After 5 days had passed, the ache was completely extinguished.

EXAMPLE 7

Figure 6:
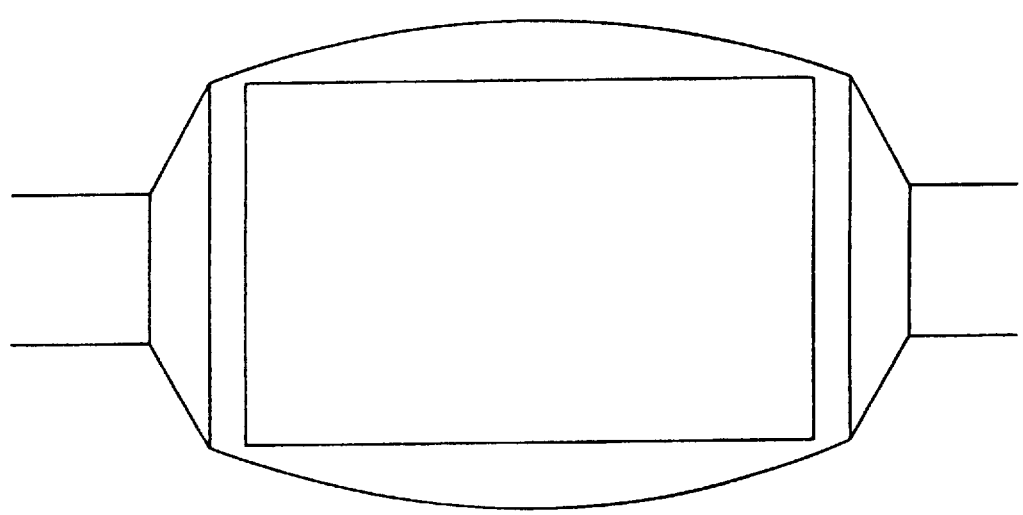
FIG. 6 is a partially schematic illustration of another magnetic belt.

In this Example, a cloth made of magnetic fiber having a size of 14 cm (length)×20 cm (width) was arranged to prepare a magnetic belt, as shown in FIG. 6. A mean strength of magnetism applied was approximately 10 gauss.

The name of a disease was osteoarthritis of the spine. The patient was a male of 51 years old, suffering from a low back pain from October 1992.

The magnetic belt was applied around the waist (4) as shown in FIG. 3. After 15 days had passed, the low back pain was completely extinguished.

What is claimed is:

1. A method for alleviating pain in a portion of a human body which comprises contacting that portion of the body with a magnetic material contained in fibers of a cloth or in a resin and applying a magnetic field of 2 or more to 20 or less gauss to that portion of the body until the pain is reduced.

2. A method for alleviating pain in a portion of a human body according to claim 1, wherein the pain is arthritis.

3. A method for alleviating pain in a portion of a human body according to claim 1, wherein the pain is low back pain.

4. A method for alleviating pain in a portion of a human body according to claim 1, wherein the pain is elbow pain.

5. A method for alleviating pain in a portion of a human body according to claim 1, wherein the pain is osteoarthritis.

* * * * *